United States Patent [19]

Elsheikh

[11] Patent Number: 4,827,055
[45] Date of Patent: May 2, 1989

[54] PROCESS FOR PREPARING VINYLIDENE FLUORIDE BY THE DIRECT FLUORINATION OF VINYLIDENE CHLORIDE

[75] Inventor: Maher Y. Elsheikh, Tredyffrin, Pa.

[73] Assignee: Pennwalt Corporation, Philadelphia, Pa.

[21] Appl. No.: 167,665

[22] Filed: Mar. 7, 1988

[51] Int. Cl.⁴ .................... C07C 17/20; C07C 21/18
[52] U.S. Cl. .................................................. 570/160
[58] Field of Search ...................................... 570/100

[56] References Cited

U.S. PATENT DOCUMENTS

| | | | |
|---|---|---|---|
| 2,670,388 | 2/1954 | Miller et al. | 570/160 |
| 2,885,449 | 5/1959 | Stahl et al. | 570/160 |
| 3,086,064 | 4/1963 | Cohen | 570/160 |
| 3,178,483 | 4/1965 | Christoph et al. | 260/653.4 |
| 3,258,500 | 6/1966 | Swamer et al. | 260/653.7 |
| 3,600,450 | 8/1971 | Kaess et al. | 260/653.3 |
| 3,723,549 | 3/1973 | Kaess et al. | 260/653.3 |
| 3,862,995 | 1/1975 | Martens et al. | 200/653.6 |
| 4,147,733 | 4/1979 | Fiske et al. | 260/653.4 |

*Primary Examiner*—J. E. Evans

[57] ABSTRACT

Vinylidene fluoride is produced by the gaseous phase reaction of vinylidene chloride with hydrofluoric acid at a temperature of from about 400° to 700° C. in the presence of oxygen and a catalyst containing AlF₃ either alone or in combination with a transition metal fluoride selected from iron, cobalt, chromium, nickel, zinc and combinations thereof.

15 Claims, No Drawings

PROCESS FOR PREPARING VINYLIDENE FLUORIDE BY THE DIRECT FLUORINATION OF VINYLIDENE CHLORIDE

BACKGROUND OF THE INVENTION

Vinylidene fluoride is a useful monomer in the preparation of fluorocarbon polymers which have excellent weathering and chemical resistant properties. Vinylidene fluoride is currently manufactured on an industrial scale by the dehydrochlorination of 1,1-difluoro-1-chloroethylene (142b) which must first be prepared by the fluorination of 1,1,1-trichloroethane. Such a multi-step process is typical for vinylidene fluoride preparation. A one-step process for converting vinylidene chloride, a readily available material, to vinylidene fluoride by gas phase reaction with HF using chromium salts or a combination of AlF$_3$ and a "activator" selected from La(NO$_3$)$_3$, NH$_4$VO$_3$, and SnCl$_2$ has been disclosed in U.S. Pat. No. 3,600,450. Unsatisfactory results were reported when AlF$_3$ was impregnated with metals such as cadmium, chromium, iron, manganese, molybdenum, nickel, zinc, or zirconium. Another process for catalytically converting vinylidene chloride is disclosed in U.S. Pat. No. 4,147,733 using an alumina based catalyst coated with Cr$_2$O$_3$ and NiO. This process uses highly corrosive aqueous HF as the fluorinating agent.

This invention provides a process for the one-step gas phase conversion of vinylidene chloride to vinylidene fluoride using anhydrous AlF$_3$, or a combination of AlF$_3$ with certain transition metals, as catalyst. These catalysts which have theretofore not been considered useful for such conversions are effective when oxygen is added to the reactant mixture.

BRIEF SUMMARY OF THE INVENTION

In accordance with this invention there is provided a process for the preparation of vinylidene fluoride comprising reacting vinylidene chloride with HF in the gaseous phase at a temperature of from about 400° C. to 700° C. in the presence of oxygen and a catalyst containing anhydrous AlF$_3$. The AlF$_3$ can be used either alone or in combination with a transition metal fluoride selected from iron, cobalt, chromium, nickel, zinc and combinations thereof.

DETAILED DESCRIPTION

In the process of the invention vinylidene chloride is directly fluorinated to vinylidene fluoride according to the following reaction:

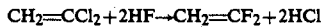

The product vinylidene fluoride is recovered from the reaction mixture by conventional techniques.

The anhydrous AlF$_3$ catalyst for use in the process of the invention can be prepared by reacting alumina with aqueous HF to precipitate the powdered hydrate AlF$_3\cdot$9H$_2$O. This hydrate when air dried at room temperature loses water to give AlF$_3\cdot$3H$_2$O. Heating the latter hydrate (100° C.–175° C.) provides anhydrous AlF$_3$ which is then ground and sieved to provide the desired particle size fraction for use as a catalyst, for example, 60–100 mesh.

The AlF$_3$ can also be combined with a transition metal fluoride selected from iron, cobalt, chromium, nickel and zinc. The catalyst can contain up to about 30wt% (7.5 to 10 wt % preferred) of transition metal based on the weight of aluminum fluoride. The combination catalysts are prepared by adding an aqueous solution of transition metal salt or salts either before, during or after the addition of the alumina to an aqueous HF solution. The precipitated material is recovered, dried and then heated at temperatures from 100° to 175° C. in one or more stages to provide the anhydrous AlF$_3$/transition metal fluoride combination catalyst which is then ground and sieved to the desired particle size.

In operation, the catalyst is loaded into a reactor tube which is formed from a hydrogen fluoride resistant material, preferably nickel or a high nickel alloy such as "Hastelloy C". The catalyst is activated by heating the reactor tube at temperatures from about 400°–700° C. (preferbaly about 650° C.) and passing air or oxygen through the catalyst for from about 2 to 72 (preferably about 60) hours. Additionally, anhydrous HF can be passed through the catalyst at room temperature up to about 600° C. for from about 2 to 72 hours. Nitrogen is usually included with the oxygen or HF stream during activation.

The process of the invention is carried out using a reactor fitted with inlets for reactant and carrier gases and equipped with means such as a single or multi-zone furnace for heating the reactor and the catalyst to controlled temperatures. The reactant gases are passed through the catalyst bed, which is heated to form about 400° to 700° C. (preferably 575° to 675° C.), at a rate to provide contact times of from about 1 to 60 seconds and preferably from about 8 to 15 seconds.

The molar ratio of HF and VCl$_2$ reactants can range from about 2:1 to about 10:1. Nitrogen in amounts of up to about 80 percent by volume of total gas flow can be used as a carrier gas.

In the absence of oxygen the amount of VF$_2$ produced, even with fresh catalyst, is generally less than about 5 mol percent (except in the case of a FeF$_3$/AlF$_3$ catalyst where a 90 mol percent initial conversion to VF$_2$ was achieved but which dropped to 16 mol percent after 1 hour). The major byproduct of the reaction is 1,1,1-trifluoroethane (143a). Adding oxygen (either neat or air) to the reaction mixture dramatically improves the results as shown in the following Examples. Amounts of from about 1 to 160 mole percent oxygen based on the amount of vinylidene chloride have been found to increase both the amounts of VF$_2$ produced and the catalyst lifetime. However, because amounts of over about 25 mole percent oxygen cause the formation of oxygenated byproducts and a lowering of the mass balance below 90% due to burn-off, preferably from about 1 to 25 mole percent and most preferably, from about 1 to 10 mole percent O$_2$, based on the moles of vinylidene chloride, is used.

Although the presence of oxygen also extends the time of high efficiency catalyst operation, when the conversion of VCl$_2$ to VF$_2$ falls below a selected level, such as about 35 percent, the catalyst efficiency can be readily restored by discontinuing the flow of HF and VCl$_2$ and passing oxygen or air through the reactor for about 1–8 hours while maintaining the catalyst temperature at 500° C. to about 700° C.

The invention is further illustrated by, but is not intended to be limited to, the following Examples wherein parts are parts by weight unless otherwise indicated.

EXAMPLE 1

A 7.5 wt % FeF$_3$/AlF$_3$ catalyst was prepared and evaluated in the conversion of VCl$_2$ to VF$_2$ in the prsence of oxygen. Alumina (200 gs, 1.96 mol) was added portionwise to a magnetically stirred solution of 52% by weight aqueous HF (500 ml, 15 mol). Addition was controlled to keep the temperature of the reaction mixture between 40° and 45° C. The addition took seven hours and the milky suspension was left at room temperature overnight. Upon standing, a fine powder of AlF$_3$.9H$_2$O precipitated. A solution of 37.5 g FeCl$_3$ (.23 mol) in 20 ml H$_2$O was added gradually to the mechanically stirred aqueous AlF$_3$ mixture. The solution turned a light violet color, the stirring was continued for four hours and the mixture was left to settle at room temperature overnight. The product precipitate was filtered and washed with acetone several times until the filtrate was acid free. The solid obtained was dried in air at room temperature and was heated at 100° C./2 hrs., 150° C./2 hours and finally at 175° C./16 hrs. The FeF$_3$/AlF$_3$ catalyst was ground using a mortar and pestle and was sieved. The 60 to 100 mesh particles were collected and used to fill a nickle, fixed bed reactor (1" O.D.×12") which was heated using a single zone furnace. The catalyst was activated at 414° C. with a 72 cc/minute (m) flow of nitrogen through the reactor for 2½ hours. The reactor temperature was then increased to 600° C., and a mixture of nitrogen (70cc/m) and anhydrous HF gas (0.04 g/m) was fed for 18 hours. Next VCl$_2$ liquid (0.04 g/m) and anhydrous liquid HF 0.02 g/m were vaporized separately and fed as gases into the reactor together with nitrogen (129 cc/m) and oxygen (15 cc/m, 162 mol % based on VCl$_2$). After scrubbing and drying the gaseous products using 16% by weight KOH solution and anhydrous CaSO$_4$ respectively, the resulting product stream was analyzed on-line using a gas chromatograph which sampled automatically. Under these conditions, the product stream contained 80 mole % VF$_2$ product together with 20 mole % of an unidentified product believed to be 1,1-difluoroethylene oxide. An 80% mass balance was calculated using a wet test meter. The reaction conditions and results are summarized in Table 1 below.

EXAMPLE 2

A 7.5 wt % ZnF$_2$/AlF$_3$ catalyst was prepared and evaluated in the conversion of VCl$_2$ to VF$_2$ in the presence of oxygen. To a stirred solution of 500 ml aqueous HF (52%–55%) by weight was added 200 grams of alumina in portions at a rate sufficient to maintain the solution temperature between 40°–45° C. After the addition was completed the suspension was left to precipitate overnight. To the precipitated AlF$_3$ was added a solution of ZnCl$_2$ (35 gm in 20 ml of water) with continuous stirring. The reaction mixture was left to settle overnight and then filtered. The precipitate was washed several times with acetone until the filtrate was neutral to litmus paper. The solid was collected, air dried and heated in an oven at 250° C. for 18 hours. The solid ZnF$_2$/AlF$_3$ catalyst was ground using a mortar and pestle. The ground material (42 g) was loaded in a 1" O.D.×12" nickel reactor which was heated using a single zone furnace. The catalyst was activated by feeding a mixture of nitrogen (100 cc/m) and hydrogen fluoride (0.13 g/m) for four hours at 100° C. The reactor temperature was raised to 665° C. and VCl$_2$ (0.02 g/m), anhydrous HF (0.025 g/m), nitrogen (80 cc/m) and oxygen (1.5 cc/m, 32 mol % on VCl$_2$) were fed to the reactor. The product stream was scrubbed, dried and analyzed as in Example 1. The product distribution in the product stream was 38 mole percent VF$_2$ and 61 mole percent 143a. The process conditions and results are summarized in Table 1 below.

EXAMPLES 3-5

Three catalysts containing 7.5 wt % of either CrF$_3$, CoF$_2$ or NiF$_2$ combined with AlF$_3$ were prepared and evaluated following the procedure described in Example 2. The process parameters and results obtained are set out in Table 1 below. The mol % O$_2$ on VCl$_2$ for Examples 3-5 was 9, 78 and 102 respectively.

TABLE 1
SUMMARY OF CATALYST EVALUATIONS IN THE PRESENCE OF OXYGEN

| | | Experimental Conditions | | | | | | | Product Distribution (Mole %)[3] | | | | | |
|---|---|---|---|---|---|---|---|---|---|---|---|---|---|---|
| Ex | Catalyst | Catalyst Density (g/cc) | N$_2$ Flow (cc/m) | O$_2$ Flow (cc/m) | VCl$_2$ Flow (g/m) | T[1] (°C.) | P (psig) | HF/ VCl$_2$ | Contact Time[2] (Sec) | VF$_2$ | 143a | unk* | CO$_2$ | Cat.[4] L.T. | Mass Bal. |
| 1. | FeF$_3$/AlF$_3$ | .47 | 129 | 15 | .04 | 620 | 7.5 | 2:1 | 13 | 80 | — | 20 | 0 | 1½ hr | 80 |
| 2. | ZnF$_2$/AlF$_3$ | .45 | 80 | 1.5 | .02 | 665 | 2.5 | 5:1 | 16 | 38 | 61 | — | 0 | 2 hrs | — |
| 3. | CrF$_3$/AlF$_3$ | .44 | 129 | 1.5 | .07 | 576 | 10.0 | 2:1 | 25 | 53 | 47 | — | 0 | 1 hr | — |
| 4. | CoF$_2$/AlF$_3$ | .46 | 129 | 9 | .05 | 630 | 6 | 2:1 | 17 | 54 | 2.9 | 40.3 | 2.7 | 2 hrs | 90 |
| 5. | NiF$_2$/AlF$_3$ | .44 | 129 | 19 | .08 | 639 | 2.5 | 2.6:1 | 13 | 43 | 27 | 28.7 | 0 | 1 hr | 89 |

*Unknown possibly 1,1-difluoroethylene oxide
[1]The temperature reported is the middle temperature of the reactor.
[2]Contact Time = $\frac{\text{total volume of gas flow/min}}{\text{volume of the catalyst bed}}$ at the reaction temperature and pressure
[3]The highest observed selectivity for VF$_2$ is reported.
[4]Cat. L.T. = Catalyst lifetime is the time of reaction during which the VF$_2$ selectivity is over 35%.

EXAMPLES 6 AND 7

In order to provide a comparison between the process of the invention using an oxygen containing carrier gas and the prior art process without oxygen, the 7.5 wt % NiF$_2$/AlF$_3$ and 7.5 wt % CoF$_2$/AlF$_3$ catalysts were evaluated. The process parameters and results are reported in Tables 2 and 3 below.

TABLE 2

EFFECT OF OXYGEN AS A CO-CARRIER GAS USING
$NiF_2/AlF_3$ CATALYST
Reaction Conditions: T = 620–630° C., $HF/VCl_2$ 2:1,
HF Flow Rate = .033 g/m, $VCl_2$ Flow Rate = 0.07 g/m, $N_2$ = 129 cc/m

| Example | $O_2$ ccm | $M_{O2}/M_{VCl2}$ | Mol % $VF_2$ | Mol % 143a | Mol % Unkown | % Mass Balance | Contact Time Seconds |
|---|---|---|---|---|---|---|---|
| Control | 0 | 0 | 4.4 | 95.6 | — | 80 | 17.2 |
| 6a | 10 | .34 | 36.5 | 45 | 18 | 74 | 15 |
| 6b | 19 | .96 | 43 | 27 | 28.7 | 89 | 13 |

TABLE 3

EFFECT OF OXYGEN AS A CO-CARRIER GAS USING
$CoF_2/AlF_3$ CATALYST
Reactor Conditions: T = 620° C., $HF/VCl_2$ 2:1,
HF = .03 g/m, $VCl_2$ = .07 g/m, $N_2$ = 129 cc/m

| Example | $O_2$ ccm | $M_{O2}/M_{VCl2}$ | mol % $VF_2$ | mol % 143a | mol % Unknown | % Mass Balance | Contact Time Seconds |
|---|---|---|---|---|---|---|---|
| Control | 0 | 0 | 6 | 94 | 0 | 85 | 17 |
| 7a | 3 | .17 | 9 | 91 | 0 | — | 17 |
| 7b | 9 | .76 | 54 | 5.6 | 40 | 90 | 17 |

EXAMPLE 8

Preparation and Evaluation of 7.5 Wt % $FeF_3/AlF_3$,
Effect of Activation and Temperature The catalyst was prepared by the identical method used in Example 1. The ground 60 to 100 mesh particles were collected and loaded into the 1"×2" nickel, fixed bed reactor. The catalyst was gradually heated (100° C./1 hour) to 650° C. using 20 cc/m of air and was maintained at this temperature for two and one half days. The temperature of the reactor was then lowered to 550° C. and a mixture of HF 0.035 g/m together with nitrogen 20 cc/m was fed for 24 hours. A reactant mixture of $VCl_2$ (0.07 g/m), HF (0.03 g/m), nitrogen (16 cc/m) and oxygen (1.2 cc/m, 6 mole % on $VCl_2$) was then fed to the reactor. A gradual increawse in both conversion of the $VCl_2$ and selectivity of $VF_2$ was obtained by increasing the temperature, e.g. at 550° C. conversion was 29% and $VF_2$ selectivity was 12.8%. At 625° C., conversion of the $VCl_2$ was 100% and selectivity for $VF_2$ was 66%. The catalyst was continuously used for a total of 62 hours without any sign of catalyst deactivation or deteriorioation. Table 4 summarizes the results of the catalyst performance between 550° C. and 625° C.

TABLE 4

Summary of the 7.5% $FeF_3/AlF_3$ Catalyst,
After Two and a Half Days of Catalyst Activation
HF = .03 g/m: $VCl_2$ = .07 g/m; $N_2$ = 16 cc/m; $O_2$ = 1.2 cc/m

| T° C. | % Conversion | % Selectivity $VF_2$ | 143a | VClF | Other |
|---|---|---|---|---|---|
| 550° C. | 29 | 12.8 | 67.4 | 17.6 | 1 |
| 600° C. | 100 | 52.6 | 43.3 | 2.6 | .4 |
| 625° C. | 100 | 66 | 37.2 | 0 | 0 |

The same catalyst was activated under different conditions, e.g., at 550° C. using 20 cc/m of air for 24 hours, followed by HF activation (0.035 g/m) for 24 hours, under these conditions, selectivity was only 1% for $VF_2$ using the same reactor feed at a reaction temperature of 550° C. The results listed in Table 5 indicate that air activation of the catalyst at a higher temperature for a longer time provided a significant improvement in selectivity under comparable reaction conditions. Therefore, it is preferred to use high temperatures (650° C. or above) and air (60 hours) to activate the catalyst.

TABLE 5

Catalyst Selectivity, Effect of the Time and
Temperature of Air Activation
7.5 Wt % $FeF_3/AlF_3$.

| Method of Activation | % $VF_2$ Selectivity |
|---|---|
| 550° C., 20 cc/m/24 hours | 1% |
| 650° C., 20 cc/m/60 hours | 12.8% |

EXAMPLE 9

Alumina (200 g) was added portionwise to a stirred solution of 52 % by weight aqueous HF (500 ml). Addition was controlled in such a way to keep the solution temperature between 40° and 45° C. After complete addition (7 hours), the milky reaction mixture was left to cool down to room temperature without stirring and $AlF_3.9H_2O$ precipitated. The solid was recovered on a filter and washed several times with acetone until it tested neutral with litmus paper. The collected solid was air dried at room temperature to give $AlF_3.3H_2O$, which was then heated in stages, e.g. 100° C./2 hours, 150° C./2 hours and finally at 175° C. for 18 hours. The resulting anhydrous material was ground with a mortar and pestle. The fine powder obtained was sieved and a 60 to 100 mesh fraction of the anhydrous $AlF_3$ particles were evaluated for catalytic activity as described below. The aluminum fluoride (31 g) was placed in the middle 4" of a 1" O.D.×12" Monel reactor. The gas inlet tube for the reactants extended directly to the catalyst powder. The bottom 4" of the reactor was filled with nickel alloy chips which were separated from the catalyst powder using an 80 mesh screen. Under these conditions, the temperature range over the length of the catalyst bed was 30° C. with the maximum temperature equal to 560° C. The catalyst was activated at 650° for 24 hours using 20 cc/m flow of air, followed by HF activation, (0.035 g/m for 24 hours at 550° C. using 20 cc/m of nitrogen as a co-carrier gas). $VCl_2$ was separately vaporized and then combined with 17 cc/m of nitrogen and 0.6 cc/m (3.7 mole % of the $VCl_2$ feed) of $O_2$ at the top of the reactor and the mixture passed through the catalyst bed together with HF at a reaction temperature of 557° C. The flow of $VCl_2$ was 0.07 grams/minute and the flow of HF was 0.03 grams/minute. The mol percent conversion of $VF_2$ increased with reaction time to a maximum at 10 hours as shown in Table 6.

TABLE 6

PRODUCT DISTRIBUTION USING $AlF_3$ AS CATALYST
Contact Time 25s, $O_2$ 3% of the $VCl_2$,
$N_2$ 20% of the Total Gas Flow

| Time (hrs) | Mol % $VF_2$ | Mol % 143a |
|---|---|---|
| 2 | 24 | 76 |
| 4 | 27 | 73 |
| 6 | 35 | 65 |
| 8 | 42 | 58 |
| 10 | 54 | 46 |
| 14 | 54 | 46 |

EXAMPLE 10

Preparation and Evaluation of $CrF_3$ 4.4%/$FeF_3$ 4%/$AlF_3$ 91.6% Catalyst $CrF_3 \cdot 3H_2O$ (30 g) was dissolved in hot water (80° C.) (150 ml) in presence of 1.5 g of $SnCl_2$. To the resulting dark green solution were added 500 ml (52% by weight) of aqueous HF, followed by 20.5 g of $FeCl_3$. Subsequently, alumina (200 g) was added portionwise in such a way to maintain the temperature between 40° and 45° C. The light green solution was covered and left at room temperature. A solid separated on standing and the precipitated solid was filtered and washed several times with acetone until it was acid free. The solid was air dried for 18 hrs. and then was heated in stages in an oven at 100° C./2 hrs., 150° C./2 hrs. and finally at 175° C. for 18 hrs. The catalyst was ground using a mortar and pestle, 65 g of the sieved 60 to 100 mesh catalyst was placed in 1"×12" Hastelloy C. reactor. The catalyst was activated at 650° C. using 20 cc/m of air for 18 hrs., followed by HF activation (0.05 g/m 24 hrs). A mixture of $VCl_2$ (0.07 g/m), HF (0.03 g/m), $N_2$ 16 cc/m and $O_2$ 1.2 cc/m, was fed to the reactor. An increase in both % conversion and % $VF_2$ selectivity was obtained by increasing the temperature as found in Example 8., e.g. at 500° C., the $VF_2$ selectivity was 14.6 at 31% conversion, and, at 625° C., the $VF_2$ selectivity was 76% at 100% conversion (Table 7). The catalyst was used continuously for 60 hours without the need for regeneration.

TABLE 7

Product Distribution and % Conversion, Using 4.4 Weight % $CrF_3$ and 4 Weight % $FeFe_3$/$AlF_3$, 7% $O_2$, Contact Time 30 Seconds

| T° C. | % Conversion | % Selectivity | | | | |
|---|---|---|---|---|---|---|
| | | $VF_2$ | 143a | 142b | VClF | Other |
| 500 | 31 | 14.6 | 58.8 | .89 | 23 | 2.1 |
| 550 | 53 | 28.7 | 53.6 | .97 | 13.3 | 3.1 |
| 600 | 95.4 | 61.5 | 38.5 | 0 | 0 | 0 |
| 625 | 100 | 76.4 | 23.6 | 0 | 0 | 0 |

I claim:

1. A process for the preparation of vinylidene fluoride comprising reacting vinylidene chloride with HF in the gas phase at a temperature of from about 400° to 700° C. in the presence of oxygen and an anhydrous $AlF_3$ containing catalyst.

2. The process of claim 1 wherein the molar ratio of HF to vinylidene chloride ranges from about 2:1 to about 10:1 and the amount of oxygen ranges from about 1 to 160 mole percent based on the amount of vinylidene chloride.

3. The process of claim 2 wherein the amount of oxygen ranges from about 1 to 25 mole percent based on the amount of vinylidene chloride.

4. The process of claim 2 wherein the amount of oxygen ranges from about 1 to 10 mole percent based on the amount of vinylidene chloride, the reaction temperature is from about 575° to 625° C., and the catalyst is activated in the presence of oxygen at a temperature of from about 400° to 700° C. and in the presence of anhydrous HF at a temperature up to about 600° C.

5. The process of claim 1 wherein the catalyst is anhydrous $AlF_3$.

6. The process of claim 2 including nitrogen as a carrier gas.

7. The process of claim 1 including the step of periodically regenerating the catalyst by passing oxygen through the catalyst bed at a temperature of at least about 500° C.

8. The process of claim 1 wherein the catalyst is anhydrous $AlF_3$ in combination with an additional metal fluoride selected from iron, cobalt, chromium, nickel, zinc and combinations thereof.

9. the process claim 8 wherein the molar ratio of HF to vinylidene chloride ranges from about 2:1 to about 10:1 and the amount of oxygen ranges from about 1 to 160 mole percent based on the amount of vinylidene chloride.

10. The process of claim 8 wherein the amount of oxygen ranges from about 1 to 25 mole percent based on the amount of vinylidene chloride.

11. The process of claim 9 including nitrogen as a carrier gas.

12. The process of claim 8 including the step of periodically regenerating the catalyst by passing oxygen through the catalyst bed.

13. The process of claim 8 wherein the catalyst contains up to about 30 weight percent of the additional metal fluoride based on the weight of aluminum fluoride.

14. The process of claim 13 wherein the catalyst contains from about 7.5 to 10 weight percent of the additional metal fluoride based on the weight of aluminum fluoride.

15. The process of claim 8 wherein the amount of oxygen ranges from about 1 to 10 mole percent based on the amount of vinylidene chloride, the reaction temperature is from about 575° to 625° C. and the catalyst is activated in the presence of oxygen at a temperature of from about 400° to 700° C. and in the presence of anhydrous HF at a temperature up to about 600° C.

* * * * *